United States Patent [19]

Schaefer et al.

[11] Patent Number: 5,425,068
[45] Date of Patent: Jun. 13, 1995

[54] MEDICAL APPARATUS SUPPORT MEMBER FOR CARRYING A COMPONENT

[75] Inventors: Willi Schaefer, Erlangen; Michael Meyer, Roettenbach; Wolfgang Mittelstaedt, Neunkirchen; Lothar Heinz, Neunkirchen A. Brand, all of Germany

[73] Assignee: Siemens Aktiengesellschaft, Munich, Germany

[21] Appl. No.: 56,759

[22] Filed: May 4, 1993

[30] Foreign Application Priority Data

May 5, 1992 [DE] Germany .................. 42 14 858.8
Nov. 6, 1992 [DE] Germany .................. 42 37 571.1

[51] Int. Cl.⁶ ............................................. A61B 6/02
[52] U.S. Cl. ............................... 378/197; 378/193
[58] Field of Search ............... 378/193, 196, 197, 167,
378/187, 189; 128/653.1, 653.5, 24 EL;
248/560, 580, 634, 635, 637; 601/4

[56] References Cited

U.S. PATENT DOCUMENTS

| 3,897,345 | 7/1975 | Foster . | |
|---|---|---|---|
| 4,017,924 | 4/1977 | Higgs . | |
| 4,636,729 | 1/1987 | Maurer et al. | 324/318 |
| 4,821,804 | 4/1989 | Pierce . | |
| 4,866,752 | 9/1989 | Bock et al. | 378/193 X |

FOREIGN PATENT DOCUMENTS 8905588  9/1988  Germany .
8812895  4/1989  Germany .

*Primary Examiner*—David P. Porta
*Attorney, Agent, or Firm*—Hill, Steadman & Simpson

[57] ABSTRACT

A support member for at least one piece of heavy medical equipment in a medical diagnostic station is made of fiber-reinforced plastic, and has a cross section which is longer in one direction than the other. The fiber-reinforced plastic serves as a shell surrounding a molding member, which may be lightweight plastic material, such that the fiber-reinforced plastic bears the loading on the member. The support member may be disposed for adjustable movement along its length by having metal guides received in the rollers of a carriage.

16 Claims, 3 Drawing Sheets

MEDICAL APPARATUS SUPPORT MEMBER FOR CARRYING A COMPONENT

BACKGROUND OF THE INVENTION

This invention relates to construction of a support member for carrying a component device in a medical apparatus. In particular, the invention is directed to a lightweight, but suitably strong, support member for carrying a diagnostic device, the position of which relative to the patient would be adjustable for use in a medical diagnostics installation, such as an x-ray station.

Germany Utility Model 8 905 588 discloses an x-ray diagnostics installation having an adjustable C-bend that carries an x-ray transmitter and an image intensifier at its ends lying opposite one another as components. The C-bend is adjustably seated along its circumference by a mount that is located at the lower end of a telescoping column. The upper end of the telescoping column is movable along a ceiling rail.

German Utility Model 8 812 895 discloses a portable medical apparatus. This apparatus also comprises a C-bend that is adjustably seated by a mount along its circumference and carries an x-ray radiator and a radiation receiver at its ends lying opposite one another.

Presently known C-bends are manufactured of one-piece or multi-piece metal parts, preferably of aluminum, that must be rolled into a profile arc and subsequently welded together. The shaping of a straight profile part requires a great outlay for manufacture and for tools. When C-bends are manufactured of cast aluminum, they then have a high dead weight.

It is an object of this invention to construct a member for carrying a component in a medical apparatus, such as the C-bend in an x-ray installation, which has low dead weight and which can be manufactured stiff, vibration-damping, cost-beneficially and simply.

SUMMARY OF THE INVENTION

A medical apparatus support member for carrying a heavy component device, such as an x-ray transmitter, is made of fiber-reinforced plastic, rather than metal. By enabling the support member to be made of fiber-reinforced plastic, manufacture cost is reduced.

The support member is simply manufactured because the fiber-reinforced plastic surrounds a molding member. The molding member only serves the purpose of shaping, which simplifies the manufacture and improves the damping properties. The fiber-reinforced plastic surrounding the molding member assumes the bearing property.

The support member has a tubular appearance, which is oval, pill-shaped, rectangular or even triangular in cross section. As a result of this shaping in combination with fibers to be preferably stressed for tension, the support member is made strong and yet affords vibration-damping and low weight.

The support member may be fashioned C-arcuately as a C-bend for carrying a radiation transmitter at one end and a radiation receiver at the other end. The C-bend would then traditionally be adjustable along its length on a carriage having bearing mounts for holding the C-bend. In this situation, the inventive support member is formed with guide rails composed of metal, provided in the region of the greatest expanse of the cross section, to seat the C-bend in the bearing mounts. The adjustability of the support member is thus made possible with little application of force because of the low rolling friction of the low weight member.

Advantageously, the guide rails are executed as wires since they can thus be adapted to the shape of the device in an especially simple way. The bearing mounts are preferably in the form of rollers which have a V-shaped channel along their circumference. An especially precise bearing of the support member and component device is thus established.

Further advantages and details of the invention will be understood from the following description and drawings.

DETAILED DESCRIPTION OF THE PREFERRED EMBODIMENTS

Figure 1:
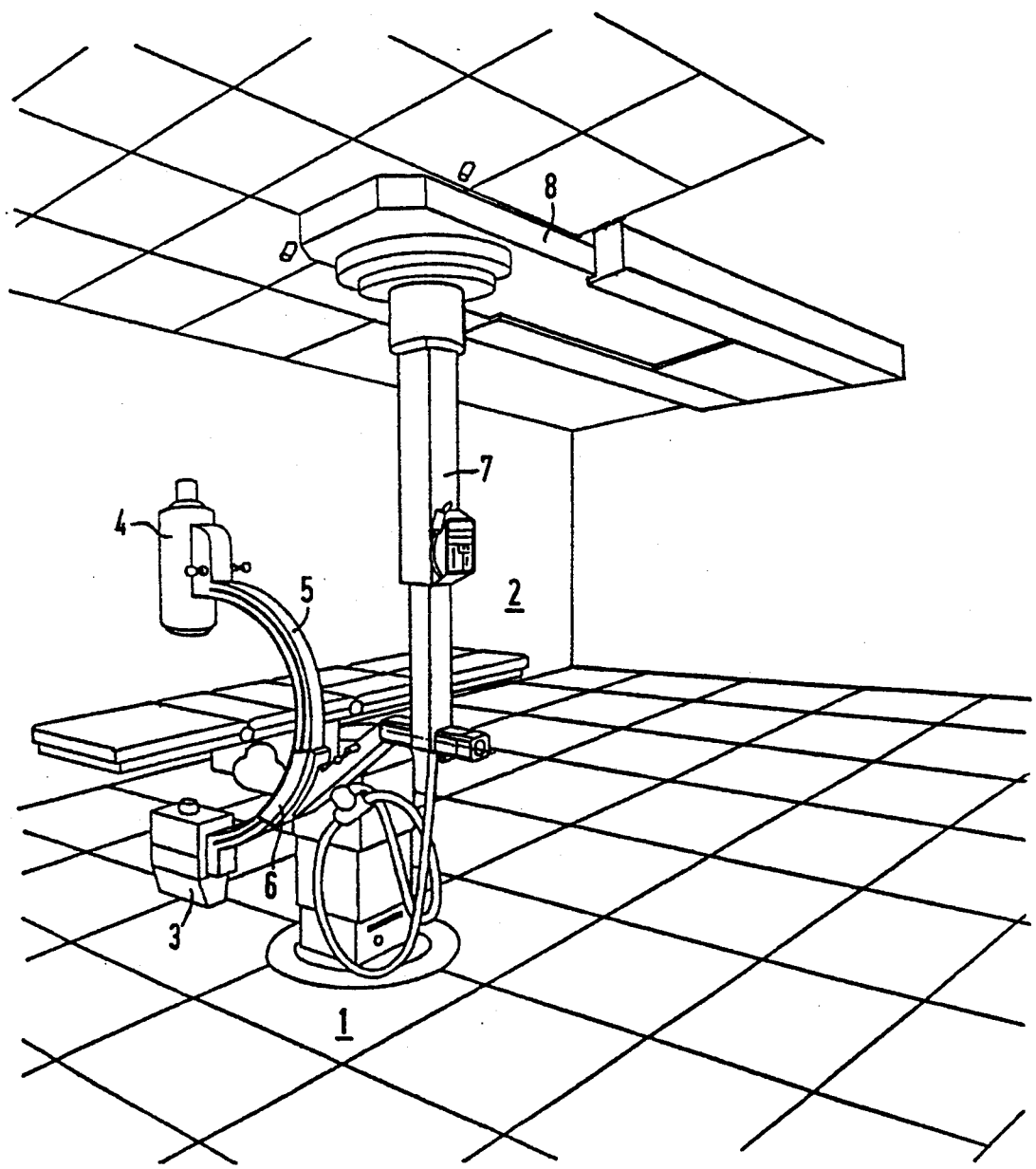
FIG. 1 is a general perspective view of the preferred application of the invention incorporated as a C-bend in a medical x-ray installation.

The invention is generally envisioned as a support member for carrying typically heavy medical component devices in a diagnostic medical installation, such as a monitor or a shock wave transmitter in a lithotriptor apparatus. The preferred application is as a C-bend in an x-ray station. Thus, FIG. 1 shows an x-ray diagnostics installation 1 have an x-ray system 2, utilizing an x-ray radiator 3 and an image intensifier 4 as a radiation receiver. A tubular C-bend 5—as part of the system 2— carries the x-ray radiator 3 and the image intensifier 4 at its ends lying opposite one another.

According to the invention, the C-bend 5 is manufactured of fiber-reinforced plastic. It thus has high stability and low weight and can be manufactured with low manufacturing outlay. The C-bend 5 is adjustably seated on a carriage 6 along its circumference.

The carriage 6 is connected to a ceiling rail 8 via a telescoping column 7, such that the carriage 6 for the x-ray radiator 3 and the image intensifier 4 is spatially adjustable within the treatment room.

Constructions of the C-bend and dispositions on the carriage in accordance with the invention are shown in FIGS. 2–5.

Figure 2:
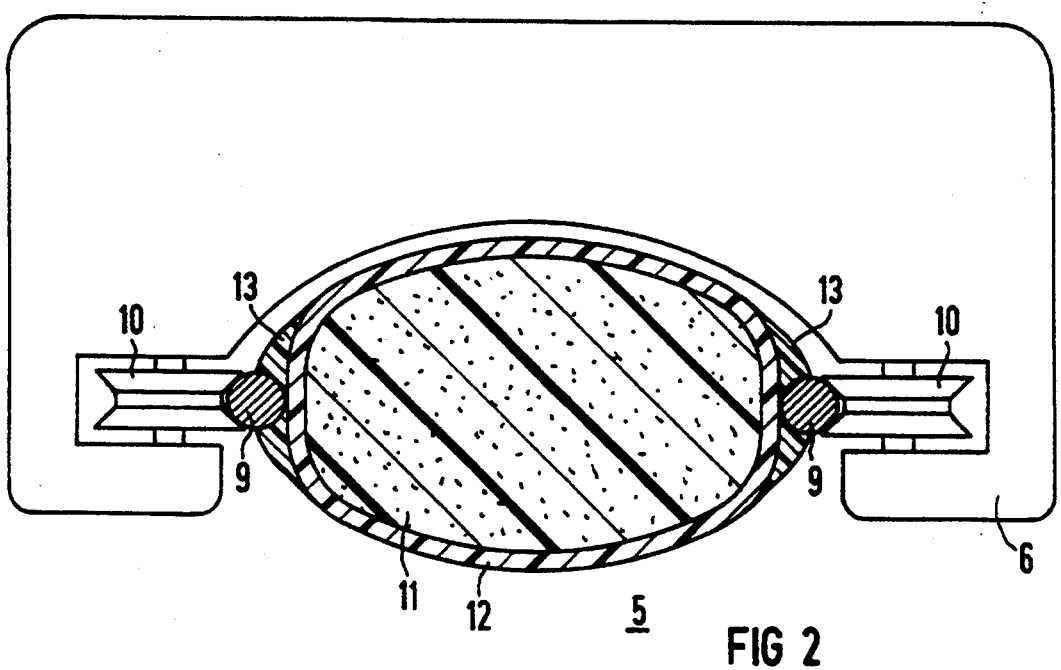
FIGS. 2–5 are each a cross sectional view of a support member constructed in accordance with the invention for use as a C-bend in a medical x-ray installation.

As shown in FIG. 2, the C-bend 5 is formed with an oval cross section. The support member, here C-bend 5, cross section may also be pill-shaped, triangular, or rectangular, thus having a greater cross sectional expanse in one direction as compared to the other.

The C-bend 5 is cost-beneficially manufactured in that a molding member 11 composed of lightweight thin plastic material or foamed plastic is surrounded by hard, fiber-reinforced plastic 12. The molding member 11 thus defines the shape; the fiber-reinforced plastic 12 assumes the bearing property. Plastics that comprise carbon, aramid or glass fibers are particularly suited as fiber-reinforced plastics.

A pair of guides 9 composed of metal are respectively provided lying opposite one another along the C-bend 5 in the region of the greatest expanse of the cross section. A carriage bearing in the form of rollers 10 support the C-bend along the guides 9. The C-bend 5 is thus seated adjustable along its length.

The guides 9 are preferably implemented as metal cables or wires that are embedded in plastic 13 that is provided in the region of the greatest expanse of the cross section of the C-bend 5. The bed for the wires can be introduced into this plastic 13 by cutting. However, it is also possible to hold the wires in the desired alignment on the fiber-reinforced plastic 12 via suitable mounts and to then apply the plastic 13 that lodges the wires.

Figure 3:
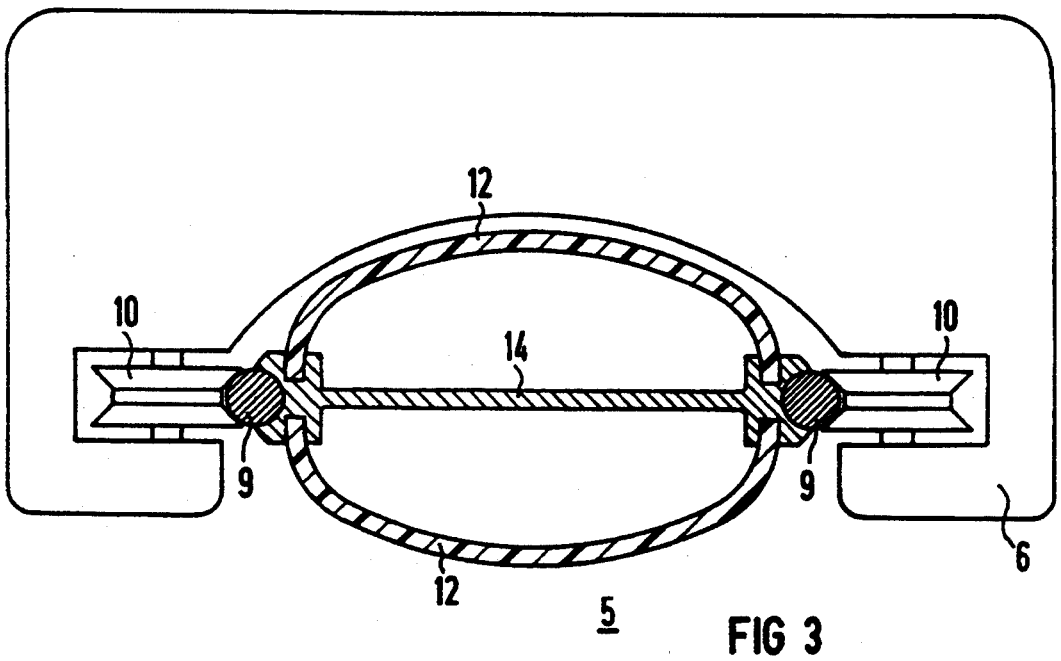

As shown in FIG. 3, a C-bend 5 can also be composed of a combination of a bent aluminum extruded profile 14 and fiber-reinforced plastic 12 within the scope of the invention. The aluminum extruded profile 14 then holds the wires. The fiber-reinforced plastic 12 surrounds the aluminum extruded profile 14 in a form that its suitable for absorbing the anticipated loads. The aluminum extruded profile 14 and the fiber-reinforced plastic 12 can be joined to one another by gluing, riveting or by being rolled in or by a combination of these possibilities. The aluminum extruded profile 14 can then comprise a small cross section, so that it can be cost-beneficially rolled and, thus, can be arcuately fashioned without great outlay.

Figure 4:
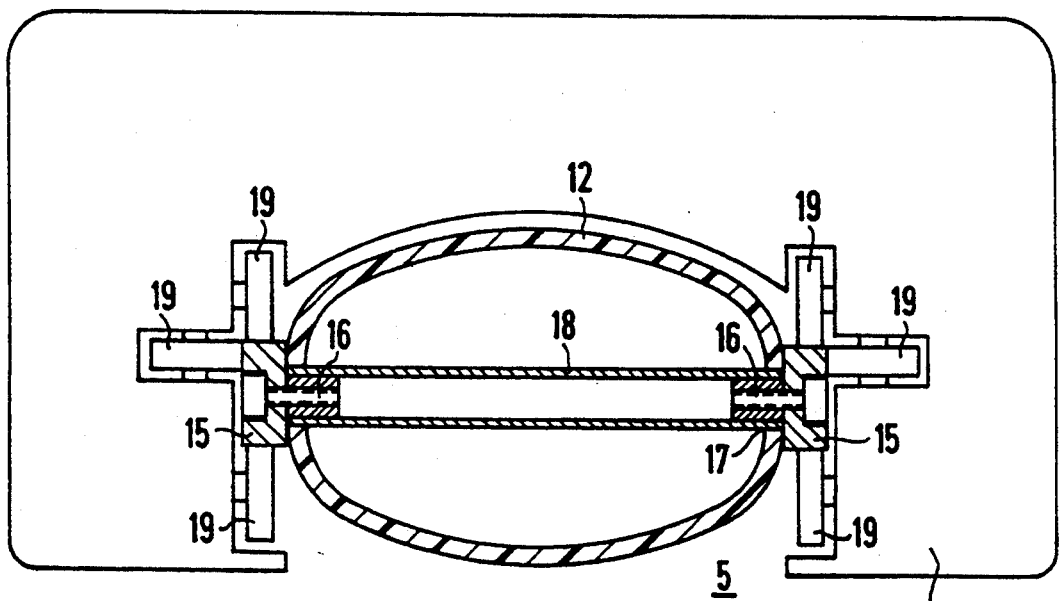

When, however, the C-bend 5 is required to have especially high stability, then a closed-form profile of fiber-reinforced plastic 12 may be manufactured, as shown by way of example in FIG. 4. Guide rails 15 are then preferably utilized. The guide rails 15 held by a screw-type connection 16 on the fiber-reinforced plastic 12. Bores 17 in the fiber-reinforced plastic 12 can be provided for this purpose, in the region of the greatest expanse of the cross section, a bushings-fitted shaft 18 of metal being introduced into these bores 17. Differing from the previous exemplary embodiments, for improved stability, there are three rollers 19 of a carriage 20 on which the C-bend 5 is guided and adjustably seated engaging at the guide rails 15.

Of course, it is also possible within the framework of the invention to manufacture other parts of the system 2 of fiber-reinforced plastic, for example the column 7 and/or the ceiling rail 8. The carriage itself can likewise be manufactured of fiber-reinforced plastic.

Figure 5:
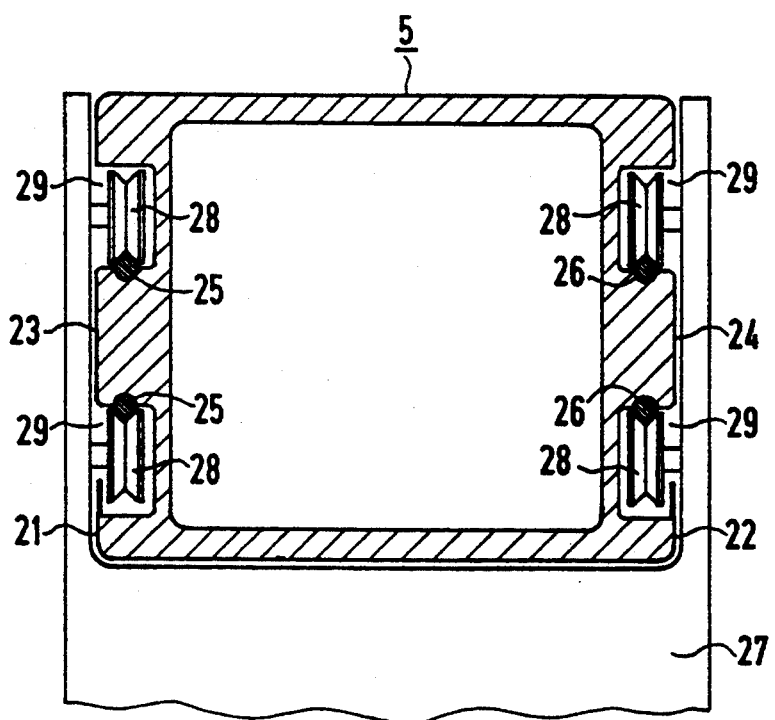

As shown in FIG. 5, a C-bend 5 has a rectangular cross section and is manufactured of a fiber-reinforced plastic. Guidewalls 23 and 24 are respectively formed at each of the longitudinally opposed ends 21 and 22 of the cross section. The guidewalls are formed of the fiber-reinforced plastic, and represent thickened areas in the fiber-reinforced plastic shell. Mounted along the transversely opposed sides of the guide walls are guides, 25 and 26 respectively, which may be in the form of metal cables or wires. A carriage 27 for the C-bend 5 carries the C-bend on bearing rollers 28, such that the C-bend is adjustably seated along its length. As noted above, it is advantageous when the guides 25, 26 are fashioned as wire having a circular cross section for the rollers 28 to have a V-shaped channel along their circumference. The rollers 28 are preferably accepted by recesses 29 formed within the profile of the C-bend 5, so that the structure is more compact.

The rollers 28 transmit forces of pressure on to relatively massive guidewalls 23, 24, such that concern for warping due to elastic material deformation is negligible. The cutting processing required for the acceptance of the round wires 25, 26 may be limited to the fashioning of half-round channels in the guidewalls 23, 24.

The spacing of the guides 25 (or, respectively, 26) relative to one another at the respective guidewalls can be accomplished within relatively narrow tolerances without difficulty since the processing can be implemented in a chucking. The distance of the guides 25 at the one side 21 of the C-bend 5 from the guides 26 at the other side 22 of the C-bend may not require any special consideration, since, for example, it could readily be arranged that the rollers 28 have no axial play at, for example, the one side 21 and the rollers 28 engaged at the other side 22 are seated in floating fashion in the axial (horizontal) direction. The rollers 28 without axial play would then absorb the vertical load component, assuming a horizontal alignment of the C-bend 5 in the carriage 27.

In an exemplary embodiment of the invention that is not shown, the recesses 29 at the respective side 21 and 22 may be joined to form a large, transverse recess having a rectangular cross section, whereby the respective guides 25 and 26 are then arranged at the outer sides of this recess.

Other embodiments and applications for the present invention will occur to those of skill in the art. It will be understood that we wish to include within the scope of our invention all such embodiments, applications, and equivalents thereof that logically and legally come within the scope of the patented claims.

We claim as our invention:

1. In a medical apparatus hoisting a heavy x-ray transmitter-weight medical device component, a support for carrying at least one said component comprising an outer shell made of fiber-reinforced plastic surrounding a molding member, said molding member serving to provide shape for said support and said shell bearing the loading on said support.

2. The support of claim 1, wherein said support has a horizontal cross section which is longer in one axis direction than in the other axis direction.

3. The support of claim 2, wherein said support has an oval-shaped horizontal cross section.

4. The support of claim 2, wherein said support is disposed for lengthwise adjustment on a carriage, said carriage having bearings to engage said support and said support having guides for movement over said bearings, said guides being formed on opposed ends of said support at the greatest expanse of its horizontal cross section.

5. The support of claim 4, wherein said support is C-arcuately shaped, and carries an x-ray transmitter for use in a medical x-ray apparatus.

6. The support of claim 4, wherein said guides are made of metal cable.

7. The support of claim 6, wherein said bearings comprise rollers formed circumferentially with V-shaped channels for receiving said metal cable therein.

8. The support of claim 6, wherein said metal cable is partially embedded in the fiber-reinforced plastic of said shell.

9. The support of claim 4, wherein said molding member includes a metal beam to which said shell is attached, said shell and said beam absorbing the loading on said support.

10. The support of claim 1, wherein said support is a column.

11. The support of claim 1, wherein said support is a ceiling rail.

12. The support of claim 1, wherein said component is an x-ray transmitter.

13. A medical apparatus utilizing a radiation transmitter and having a C-arcuately shaped support carrying said transmitter and a carriage on which said support is lengthwise adjustable, said support comprising an outer shell made of fiber-reinforced plastic surrounding a molding member, said shell bearing the loading on said support.

14. The medical apparatus of claim 13, wherein said support has a horizontal cross section which is longer in one axial direction than in the other axial direction.

15. The medical apparatus of claim 14 wherein said support is formed with guides on said shell at the opposed ends of the greatest expanse of said horizontal cross section of said support and said carriage has bearings for carrying said guides.

16. The medical apparatus of claim 15, wherein said guides are in the form of metal cable partially embedded in the fiber-reinforced plastic of said shell.

* * * * *